United States Patent
Kuhn et al.

(10) Patent No.: US 7,711,406 B2
(45) Date of Patent: May 4, 2010

(54) SYSTEM AND METHOD FOR DETECTION OF ELECTROMAGNETIC RADIATION BY AMORPHOUS SILICON X-RAY DETECTOR FOR METAL DETECTION IN X-RAY IMAGING

(75) Inventors: Paul Kenneth Kuhn, Salt Lake City, UT (US); Peter Traneus Anderson, Andover, MA (US); John Robert Lamberty, Oconomowoc, WI (US)

(73) Assignee: General Electric Company, Schenectady, NY (US)

( * ) Notice: Subject to any disclaimer, the term of this patent is extended or adjusted under 35 U.S.C. 154(b) by 650 days.

(21) Appl. No.: 11/286,954

(22) Filed: Nov. 23, 2005

(65) Prior Publication Data

US 2010/0069741 A1   Mar. 18, 2010

(51) Int. Cl.
*A61B 5/05* (2006.01)
(52) U.S. Cl. .................. 600/407; 600/424; 378/91; 378/98.7; 378/21
(58) Field of Classification Search ......... 600/407–410, 600/424; 378/91, 21, 98.7; 250/370.9
See application file for complete search history.

(56) References Cited

U.S. PATENT DOCUMENTS

| | | | | |
|---|---|---|---|---|
| 5,729,129 | A | * 3/1998 | Acker | .............. 324/207.12 |
| 5,873,822 | A | 2/1999 | Ferre | |
| 5,967,980 | A | 10/1999 | Ferre | |
| 6,084,412 | A | * 7/2000 | Guo et al. | .............. 324/336 |
| 6,175,756 | B1 | 1/2001 | Ferre | |
| 6,341,231 | B1 | 1/2002 | Ferre | |
| 6,484,049 | B1 | 11/2002 | Seeley | |

(Continued)

FOREIGN PATENT DOCUMENTS

WO   WO00/00086 A1   1/2000

OTHER PUBLICATIONS

El-Mohri, et al. "A quantitative investigation of additive noise reduction for active matrix flat-panel imagers using compensation lines," Med. Phys. 27(8):1855-1864 (Aug. 2000) XP012011235 ISSN: 0094-2405.

(Continued)

*Primary Examiner*—Long V Le
*Assistant Examiner*—Sanjay Cattungal
(74) *Attorney, Agent, or Firm*—McAndrews, Held & Malloy, Ltd.; Peter J. Vogel; Michael A. Dellapenna

(57) ABSTRACT

Certain embodiments of the present invention provide a method for detecting an electromagnetic field in an imaging system including emitting an electromagnetic field with an electromagnetic transmitter, sensing an electromagnetic field with an imaging system detector, and reading a field image from the detector based at least in part on the electromagnetic field. The imaging system detector is capable of reading an object image and a field image. The detector may be an amorphous silicon flat panel x-ray detector. The electromagnetic transmitter may be used in surgical navigation. The position of a surgical device, instrument, and/or tool may be determined based in part on the field image. The detector may be coordinated to acquire the field image when the electromagnetic transmitter is emitting an electromagnetic field. The detector may be coordinated to acquire the object image when the electromagnetic transmitter is not emitting an electromagnetic field.

7 Claims, 6 Drawing Sheets

U.S. PATENT DOCUMENTS

| | | | |
|---|---|---|---|
| 6,490,475 B1 | 12/2002 | Seeley | |
| 6,690,963 B2 * | 2/2004 | Ben-Haim et al. | 600/424 |
| 6,753,873 B2 * | 6/2004 | Dixon et al. | 345/542 |
| 6,774,624 B2 * | 8/2004 | Anderson et al. | 324/207.17 |
| 6,788,967 B2 * | 9/2004 | Ben-Haim et al. | 600/424 |
| 6,856,826 B2 | 2/2005 | Seeley | |
| 6,856,827 B2 | 2/2005 | Seeley | |
| 7,091,491 B2 * | 8/2006 | Kautzer et al. | 250/370.09 |
| 7,142,633 B2 * | 11/2006 | Eberhard et al. | 378/62 |
| 2002/0044141 A1 * | 4/2002 | Watanabe et al. | 345/204 |
| 2002/0106820 A1 * | 8/2002 | Nikawa | 438/14 |
| 2002/0165448 A1 * | 11/2002 | Ben-Haim et al. | 600/424 |
| 2005/0226375 A1 * | 10/2005 | Eberhard et al. | 378/62 |
| 2005/0254624 A1 * | 11/2005 | Kautzer et al. | 378/91 |
| 2006/0121849 A1 * | 6/2006 | Anderson | 455/41.1 |
| 2006/0154604 A1 * | 7/2006 | Anderson | 455/41.1 |

OTHER PUBLICATIONS

Oct. 24, 2007 French Patent Office Search Report and Written Opinion for French Patent Application FR 0754326.

English Translation of May 29, 2009 French Patent Office Search Report and Written Opinion for French Patent Application FR 0655224.

* cited by examiner

SYSTEM AND METHOD FOR DETECTION OF ELECTROMAGNETIC RADIATION BY AMORPHOUS SILICON X-RAY DETECTOR FOR METAL DETECTION IN X-RAY IMAGING

BACKGROUND OF THE INVENTION

The present invention generally relates to amorphous silicon x-ray detectors. In particular, the present invention relates to the detection of electromagnetic radiation by an amorphous silicon x-ray detector for metal detection in x-ray imaging.

Digital imaging systems may be used to capture images to assist a physician in making an accurate diagnosis. Digital radiography imaging systems typically include a source and a detector. Energy, such as x-rays, produced by the source travel through an object to be imaged and are detected by the detector. An associated image processing system obtains image data from the detector and prepares a corresponding diagnostic image on a display.

The detector may be an amorphous silicon flat panel detector, for example. Amorphous silicon is a type of silicon that is not crystalline in structure. Image pixels are formed from amorphous silicon photodiodes connected to switches on the flat panel. A scintillator is placed in front of the flat panel detector. For example, the scintillator receives x-rays from an x-ray source and emits light of an intensity related to the amount of x-rays absorbed. The light activates the photodiodes in the amorphous silicon flat panel detector. Readout electronics obtain pixel data from the photodiodes through data lines (columns) and scan lines (rows). Images may be formed from the pixel data. Images may be displayed in real time. Flat panel detectors may offer more detailed images than an image intensifier and camera combination. Flat panel detectors may allow faster image acquisition than an image intensifier and camera combination depending upon image resolution.

Medical practitioners, such as doctors, surgeons, and other medical professionals, often rely upon technology when performing a medical procedure, such as image-guided surgery ("IGS") or examination. An IGS system may provide positioning and/or orientation ("P&O") information for the medical instrument with respect to the patient or a reference coordinate system, for example. A medical practitioner may refer to the IGS system to ascertain the P&O of the medical instrument when the instrument is not within the practitioner's line of sight with regard to the patient's anatomy, or with respect to non-visual information relative to the patient. An IGS system may also aid in pre-surgical planning.

The IGS or surgical navigation system allows the medical practitioner to visualize the patient's anatomy and track the P&O of the instrument. The medical practitioner may use the tracking system to determine when the instrument is positioned in a desired location or oriented in a particular direction. The medical practitioner may locate and operate on, or provide therapy to, a desired or injured area while avoiding other structures. Increased precision in locating medical instruments within a patient may provide for a less invasive medical procedure by facilitating improved control over smaller, flexible instruments having less impact on the patient. Improved control and precision with smaller, more refined instruments may also reduce risks associated with more invasive procedures such as open surgery.

Tracking systems used in surgical navigation systems may be optical, ultrasonic, inertial, or electromagnetic, for example. Electromagnetic tracking systems may employ coils as receivers and transmitters. An electromagnetic tracking system may be configured in an industry-standard coil architecture ("ISCA"), for example, although other configurations for electromagnetic tracking systems may also be used. The ISCA is characterized by three colocated orthogonal quasi-dipole transmitter coils and three colocated quasi-dipole receiver coils. Other systems may use three large, non-dipole, non-colocated transmitter coils with three colocated quasi-dipole receiver coils. Another tracking system architecture uses an array of six or more transmitter coils spread out in space and one or more quasi-dipole receiver coils. Alternatively, a single quasi-dipole transmitter coil may be used with an array of six or more receivers spread out in space.

The ISCA tracker architecture uses a three-axis quasi-dipole coil transmitter and a three-axis quasi-dipole coil receiver. Each three-axis transmitter or receiver is built so that the three coils exhibit the same effective area, are oriented orthogonal to one another, and are centered at the same point. The exact sizes, shapes, and relative-to-one-another positions of the transmitter and receiver coil-trios are measured in manufacturing. If the coils are small enough compared to a distance between the transmitter and receiver, then the coil may exhibit dipole behavior. Magnetic fields generated by the trio of transmitter coils may be detected by the trio of receiver coils. Nine transmitter-receiver mutual inductance measurements may be obtained. From these nine parameter measurements and the information determined in manufacturing, a position and orientation determination of the receiver coil-trio may be made with respect to the transmitter coil-trio for all six degrees of freedom.

In medical and surgical imaging, such as intraoperative or perioperative imaging, images are formed of a region of a patient's body. The images are used to aid in an ongoing procedure with a surgical tool or instrument applied to the patient and tracked in relation to a reference coordinate system formed from the images. Image-guided surgery is of a special utility in surgical procedures such as brain surgery and arthroscopic procedures on the knee, wrist, shoulder or spine, as well as certain types of angiography, cardiac procedures, interventional radiology and biopsies in which x-ray images may be taken to display, correct the P&O of, or otherwise navigate a tool or instrument involved in the procedure.

Several areas of surgery involve very precise planning and control for placement of an elongated probe or other device in tissue or bone that is internal or difficult to view directly. In particular, for brain surgery, stereotactic frames that define an entry point, probe angle and probe depth are used to access a site in the brain, generally in conjunction with previously compiled three-dimensional diagnostic images, such as MRI, PET or CT scan images, which provide accurate tissue images. For placement of pedicle screws in the spine, where visual and fluoroscopic imaging cannot capture an axial view to center a profile of an insertion path in bone, navigation systems have also been useful.

However, metal or other materials capable of distorting electromagnetic fields in the object being imaged can result in artifacts or distortions in the image. For example, metal in the area of the patient being x-rayed, such as pedicle screws in the spine, can cause streak artifacts. These distortions or artifacts may generally reduce the value of the image to the medical practitioner.

In the case of a three-dimensional (3D) image, these distortions or artifacts may have an even more pronounced effect. 3D volumetric imaging provides new diagnostic and clinical analysis tools to physicians. 3D images are created by acquiring a series of two-dimensional (2D) images at predetermined positions along an arc about a patient. Software applications using complex mathematical processes extract volume elements or "voxels" from the 2D images by using the image content (e.g., a black-and-white x-ray image) and positional information (e.g., where the image was positioned along an arc). The voxels may then be assembled into a three-dimensional image and then viewed from any angle. Artifacts or distortions in the 2D images from, for example, metal in the object being imaged, may be amplified through the use of the 2D images to create the 3D images. This amplification occurs in part because there is less data available in the 2D images, due to the artifacts and distortions, to properly assemble the voxels for the 3D image. Metal artifact reduction algorithms may be used to reduce the effects of the distortions or artifacts caused by metal in the object being imaged. Thus, it is highly desirable to determine when metal is present in the object being imaged so that techniques such as metal artifact reduction algorithms may be utilized.

Another potential source of artifacts or distortions in images are electromagnetic fields. An electromagnetic field affecting the detector may originate in part from an electromagnetic transmitter such as, for example, an electromagnetic transmitter in a surgical navigation system. One or more parts of the detector of the imaging system may be susceptible to electromagnetic fields. For example, the photodiodes, readout electronics, and/or wiring within an amorphous silicon flat panel x-ray detector may be affected by an electromagnetic field. These components may, for example, act as an antenna. The electromagnetic field may result in distortions or artifacts in the images read from the detector in part because the electromagnetic fields introduce spurious signals or noise into one or more of the components of the detector. This noise may appear as artifacts or distortions in the images read from the detector. Thus, it is desirable to detect electromagnetic fields so that distortions and artifacts caused by such fields may be compensated for.

Therefore, there is a need for compensating for electromagnetic fields affecting amorphous silicon x-ray detectors. Further, there is a need for detecting metal in x-ray imaging by electromagnetic radiation using an amorphous silicon x-ray detector.

BRIEF SUMMARY OF THE INVENTION

Certain embodiments of the present invention provide a method for detecting an electromagnetic field in an imaging system including emitting an electromagnetic field with an electromagnetic transmitter, sensing an electromagnetic field with an imaging system detector, and reading a field image from the detector based at least in part on the electromagnetic field. The imaging system detector is capable of reading an object image. The imaging system detector is capable of reading a field image. In an embodiment, the detector is a flat panel detector, such as an amorphous silicon flat panel x-ray detector. In an embodiment, the object image is an x-ray image. In an embodiment, the electromagnetic transmitter is used in surgical navigation. In an embodiment, the method includes determining the position of at least one of a surgical device, instrument, and tool based at least in part on the field image. In certain embodiments, the electromagnetic transmitter has a transmit mode and a non-transmit mode, where the electromagnetic transmitter emits the electromagnetic field when in the transmit mode, and does not emit the electromagnetic field when in the non-transmit mode. In an embodiment, the field image is coordinated to be read when the electromagnetic transmitter is in the transmit mode. In an embodiment, the method includes reading an object image from the detector. In an embodiment, the object image is coordinated to be read when the surgical navigation device is in the non-transmit mode. In an embodiment, an electromagnetic model of a surgical navigation system is adjusted based at least in part on the field image and the object image.

Certain embodiments of the present invention provide a method for improving image quality in an imaging system including emitting an electromagnetic field with an electromagnetic transmitter, reading a first field image from an imaging system detector based at least in part on the electromagnetic field, positioning an object to be imaged by the imaging system, reading a second field image from the detector based at least in part on the electromagnetic field, and detecting the presence of metal based at least in part on at least one of the first field image and the second field image. In an embodiment, the detector is a flat panel detector, such as an amorphous silicon flat panel x-ray detector. In an embodiment, the image is an x-ray image. In an embodiment, the electromagnetic transmitter is used in a surgical navigation system. In certain embodiments, the method further includes reading an object image from the detector and processing the object image with a metal artifact reduction algorithm when metal is detected. In an embodiment, the object image is an x-ray image.

Certain embodiments of the present invention provide an apparatus for improving image quality in an imagine system that includes an imaging system detector and an image processing component. The detector is capable of acquiring a first field image, a second field image, and an object image. The image processing component is in communication with the detector. The image processing component adjusts the object image based at least in part on the first and/or second field images. In an embodiment, the detector is a flat panel detector, such as an amorphous silicon flat panel x-ray detector. In an embodiment, the object image is an x-ray image. In an embodiment, at least one of the first and second field images is based at least in part on an electromagnetic field sensed by the detector. In an embodiment, the electromagnetic field is emitted at least in part by a surgical navigation device. In an embodiment, the first field image differs from the second field image based at least in part on the presence of metal in an object being imaged by the imaging system. In certain embodiments, the image processing component utilizes a metal artifact reduction algorithm to process the object image when metal is sensed by the detector. In an embodiment, the first field image is acquired when no object is positioned to be imaged by the imaging system. In an embodiment, the second field image is acquired when an object is positioned to be imaged by the imaging system.

Figure 1:
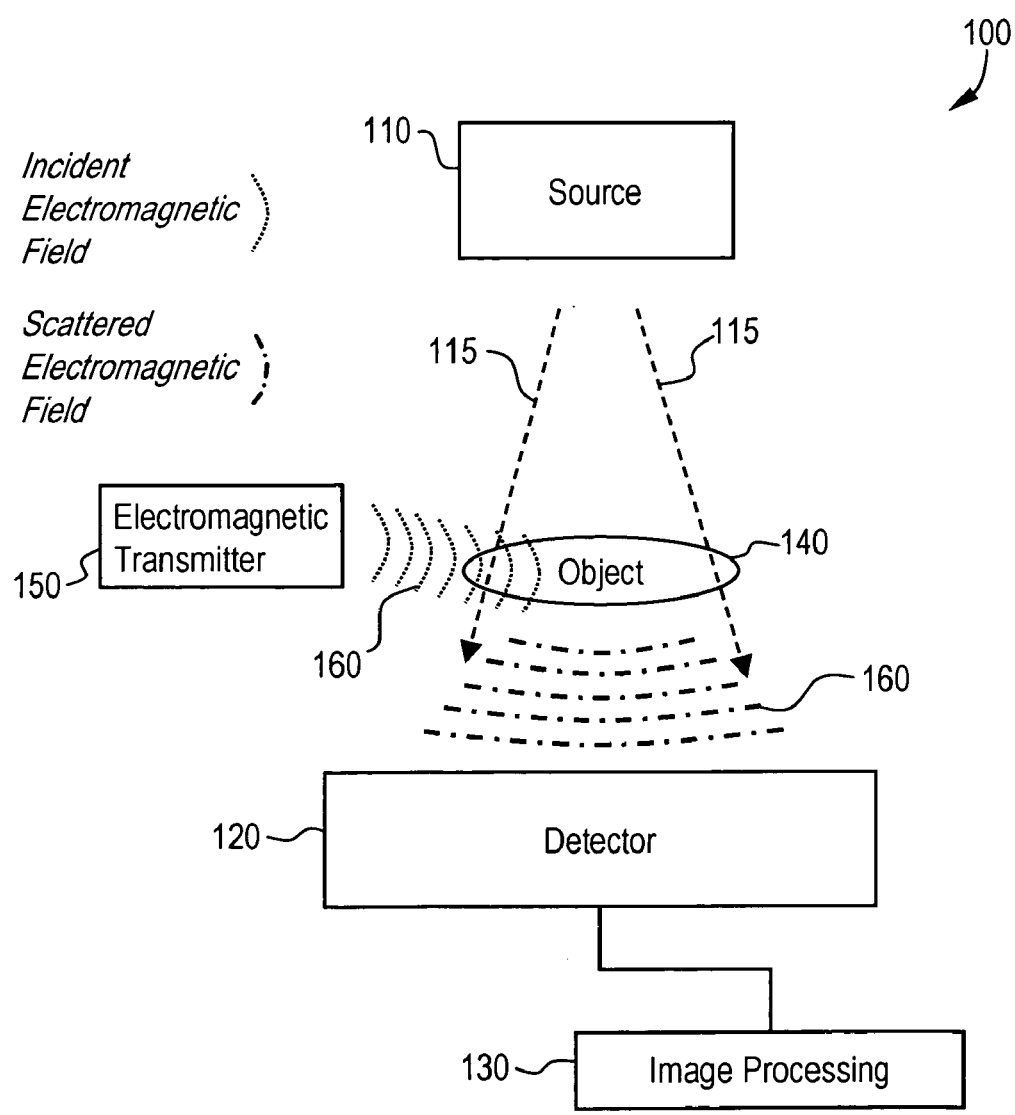
FIG. 1 illustrates an imaging system used in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates an imaging system 100 used in accordance with an embodiment of the present invention. For the purposes of illustration, the imaging system 100 is described as an x-ray system. The imaging system 100 includes subsystems such as an x-ray source 110, an x-ray detector 120, and an image processing component 130. Also, an object 140 to be imaged may be present. The imaging system 100 may also include an electronic transmitter 150.

The detector 120 may be, for example, a flat panel detector, such as an amorphous silicon flat panel x-ray detector. The detector 120 may include and/or be connected to an array of detector elements and readout electronics. The readout electronics may be part of a data acquisition component. The readout electronics are in communication with the detector elements. The components of the detector 120 may be connected by wires and/or conductors, for example. The detector 120 may be sensitive to and/or affected by electromagnetic signals based at least in part on the components described above, including, for example, the detector elements, readout electronics, and wires and/or conductors. That is, the nature of the detector may create unintended current loops. An electromagnetic field may therefore induce voltages in these loops. As a result, the detector 120 may act as an antenna for certain electromagnetic fields. A detector 120 that is a flat panel detector may be more sensitive to an electromagnetic field than, for example, an image intensifier tube detector. The readout electronics read data from the detector elements. The data read from the detector elements may represent, for example, x-ray intensity at one or more of the detector elements. This acquired data may be represented as an image. For example, the data may be represented as a 2048 by 2048 grid of pixels, each with a 16-bit value. The data read from the detector 120 may, based at least in part on the above mentioned induced voltages, alter the data and/or image acquired from the detector 120.

The object 140 may be, for example, a patient or a calibration tool. The object 140 may include metal or other material capable of distorting an electromagnetic field, for example. For example, the object 140 may be a patient that has a metal pedicle screw in his spine. As another example, the object 140 may be a patient's arm that had a fracture repaired with a metal plate and screws.

The electromagnetic transmitter 150 may be, for example, part of a surgical navigation system or device. The surgical navigation system may employ an electromagnetic tracking system, for example. The electromagnetic tracking system may be configured in accordance with, for example, the ISCA. The electromagnetic surgical navigation system or device may employ a non-ISCA navigation system. The electromagnetic transmitter 150 may be used, at least in part, to determine the position of, for example, a surgical device, instrument or tool. For example, the electromagnetic transmitter 150 may be part of a surgical navigation system for tracking the position of a probe. The electromagnetic transmitter 150 may be located on the probe and may emit an electromagnetic field to aid in determining the probe's position, for example. As another example, the electromagnetic transmitter 150 may emit an electromagnetic field that is affected by coils on the probe to determine the probe's position. In an embodiment, the electromagnetic transmitter 150 has a transmit mode and a non-transmit mode. In the transmit mode, the electromagnetic transmitter 150 emits an electromagnetic field 160 and in the non-transmit mode, the electromagnetic transmitter 150 does not emit an electromagnetic field 160.

An electromagnetic receiver (not shown) may also be present. The electromagnetic receiver may be part of a surgical navigation system or device. Alternatively, in certain embodiments, the detector 120 may act as an electromagnetic receiver. The electromagnetic receiver may, for example, receive the electromagnetic field 160 from the electromagnetic transmitter 150. The electromagnetic receiver may be configured to determine a position and/or orientation of a probe, for example.

The detector 120 may be positioned to detect energy, such as x-rays 115, emitted by the source 110. The energy, such as x-rays 115, travels from the source 110 through the object 140 to the detector 120. Energy detected at the detector 120 is representative of the structure of the object 140.

The image processing component 130 is in communication with the detector 120. The image processing component 130 can process images acquired from the detector 120. The image processing component 130 may, for example, run various image processing algorithms on an image acquired from the detector 120. Such algorithms may include metal artifact reduction algorithms. A metal artifact reduction algorithm may reduce the effect of metal in the object 140 in the image acquired from the detector 120.

An object 140 may be positioned in the imaging system 100 for imaging. The object 140 may be positioned in front of the detector 120. In one exemplary system, an x-ray source 110 is positioned above the object 140. The detector 120 is positioned below the object 140.

In operation, the x-ray source 110 emits x-rays 115. The x-rays 115 are transmitted through the object 140. The detector 120 then detects the x-rays 115. The system 100 may include a scintillator (not shown) placed between the object 140 and the detector 120. The scintillator emits light in response to the x-rays transmitted from the x-ray source 110 through the object 140. The emitted light is transmitted to the x-ray detector 120. For example, light emitted by the scintillator activates or discharges photodiodes in the detector 120.

After the detector 120 detects the energy from the source 110, the data collected by the detector elements of the detector 120 is read out as an image of the object 140. In an embodiment, this object image may be an x-ray image.

The electromagnetic transmitter 150 may emit an electromagnetic field 160. The electromagnetic field 160 may be an incident electromagnetic field or a scattered electromagnetic field. The scattered electromagnetic field may result from the presence of metal in the object 140 being imaged by the imaging system 100. The electromagnetic field 160 may be detected by an electromagnetic receiver (not shown). As described below, the electromagnetic field 160 may be detected by the detector 120.

The detector 120 may be susceptible to the electromagnetic field 160 emitted by the electromagnetic transmitter 150. That is, the electromagnetic field 160 may cause data to be registered by the detector 120 even in the absence of, for example, x-rays. This may be due to the implementation of the detector 120. For example, some of the components of the detector 120 may be unshielded from electromagnetic fields. Thus, in the presence of an electromagnetic field 160, the detector 120 may be energized or de-energized resulting in a reading of the detector showing data. This data represents information about the electromagnetic field 160 that has been sensed by the detector 120. This electromagnetic field data may be read out as an image. For example, each pixel of the field image may represent the strength (e.g., average strength) of the electromagnetic field 160 at each detector element or over a portion of the detector 120. In certain embodiments, the electromagnetic field 160 emitted by the electromagnetic transmitter 150 may be adjusted to facilitate interpreting the data included in the field image. In certain embodiments, the electromagnetic transmitter 150 may be configured to transmit in coordination with reading of the field image from the detector 120.

Figure 5:
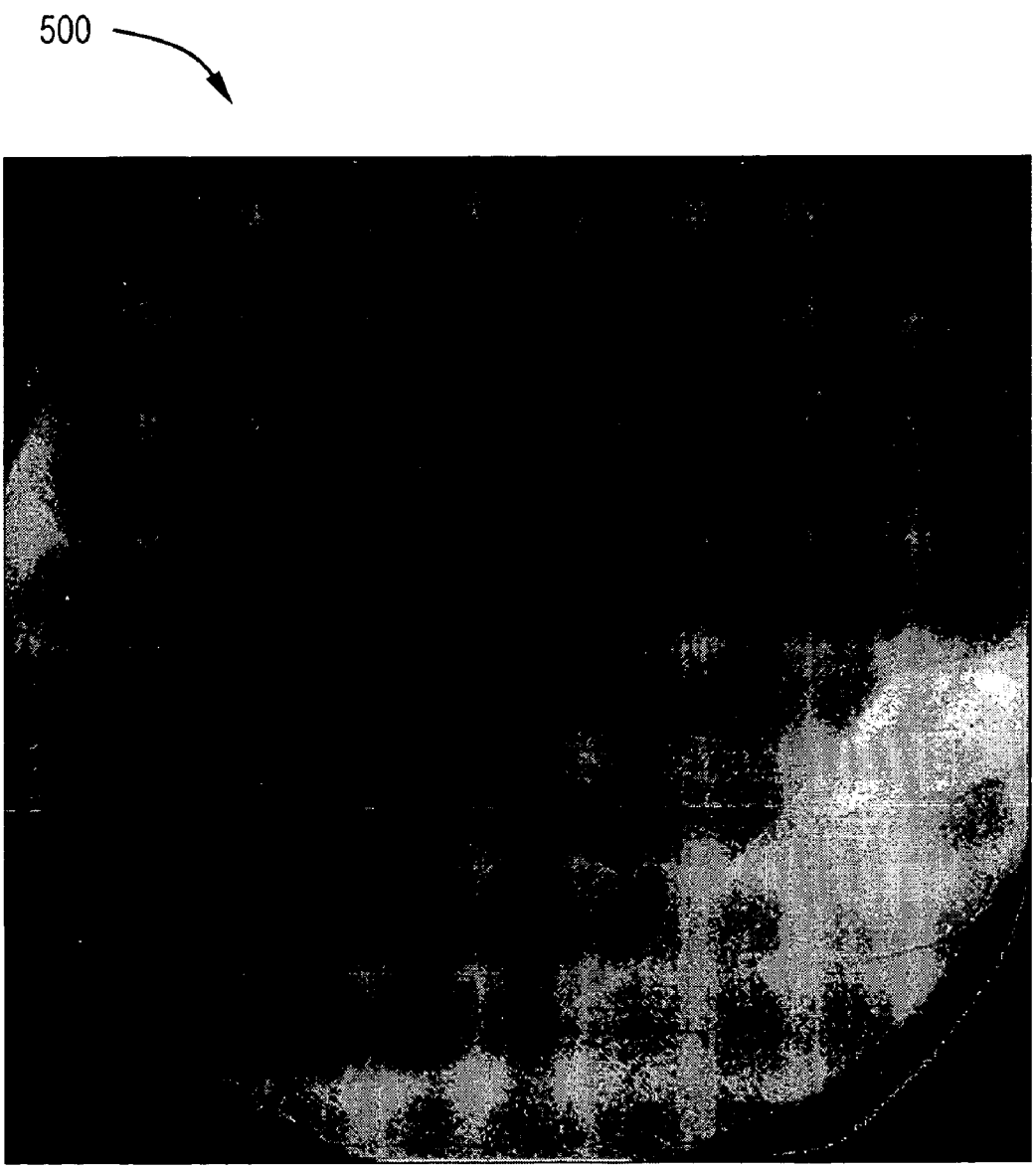
FIG. 5 illustrates an object image acquired in accordance with an embodiment of the present invention.
Figure 6:
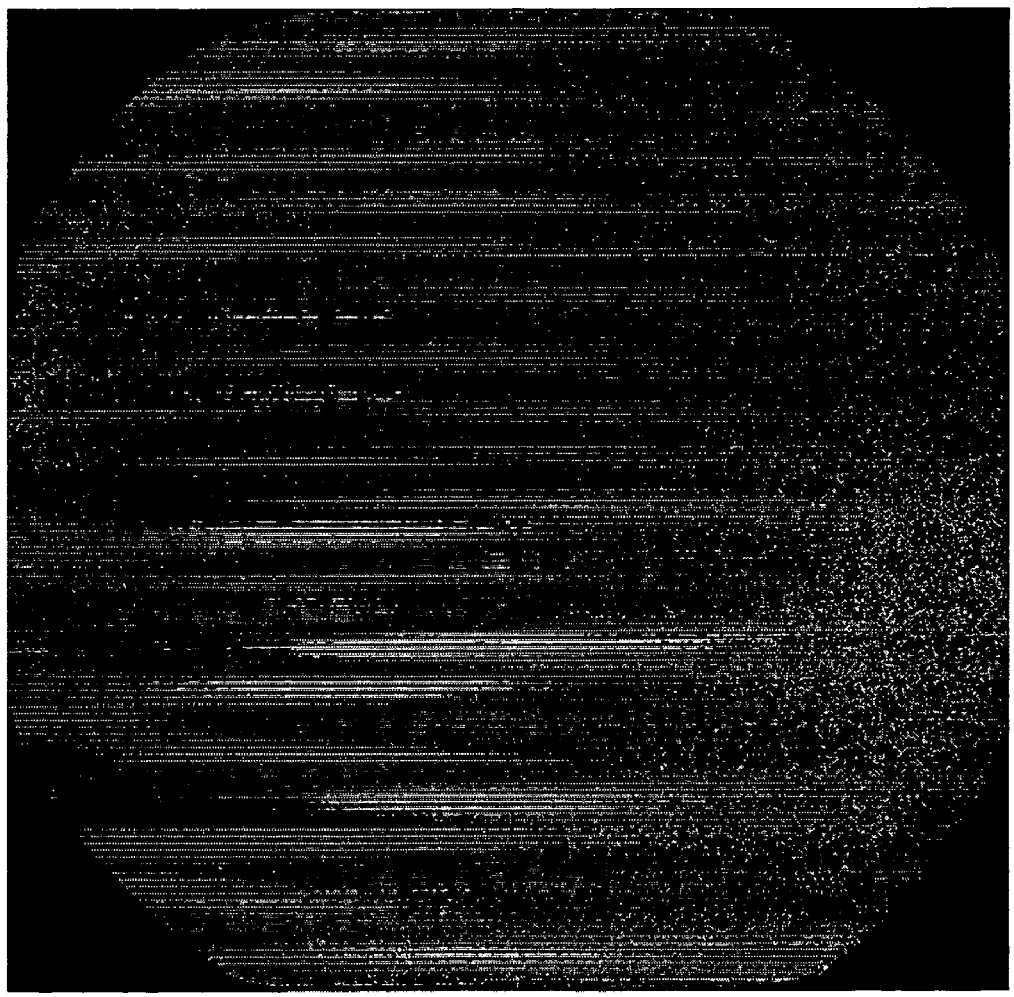
FIG. 6 illustrates a field image acquired in accordance with an embodiment of the present invention.

FIG. 5 illustrates an object image 500 acquired in accordance with an embodiment of the present invention. More specifically, the object image 500 illustrates an object image acquired when the electromagnetic transmitter 150 is not emitting an electromagnetic field 160. FIG. 6 illustrates a field image 600 acquired in accordance with an embodiment of the present invention. More specifically, the field image 600 illustrates a field image acquired when the electromagnetic transmitter 150 is emitting an electromagnetic field 160.

The field image may be read both when an object 140 is positioned in the imaging system 100 and when no object 140 is present. The object 140 may contain metal, for example. The metal in the object 140 may affect the electromagnetic field 160. The presence of metal may result in a different field image being read when an object 140 is present as compared to a field image read when no object 140 is present in the imaging system 100. Thus, metal may be detected in the object 140 by comparing a field image taken when the object 140 is not present with a field image acquired when the object 140 is present. In addition, even in the absence of metal in the object 140, a field image acquired when the object 140 is present may differ from a field image acquired when the object 140 is not present.

The image processing component 130 may be capable of running various image processing algorithms on an image acquired from the detector 120. Such algorithms may include metal artifact reduction algorithms. A metal artifact reduction algorithm may reduce the effect of metal in an image acquired from the detector 120. If metal is known to be in the object 140, a metal artifact reduction algorithm may be utilized. Metal may be detected in the object 140 based in part on one or more field images. In an embodiment, a field image may indicate a specific area in the object image that is affected by metal in the object 140. In this case, the object image may be adjusted by, for example, a metal artifact reduction algorithm, applied only to a portion of the object image potentially affected by the metal. Several methods have been proposed to reduce the artifacts caused by the presence of metal in an x-ray imaged object. As an example, one such algorithm sets threshold values to the x-ray images or projections and applies an interpolation algorithm to aid in the reconstruction of the images or projections when the thresholds are exceeded.

Figure 2:
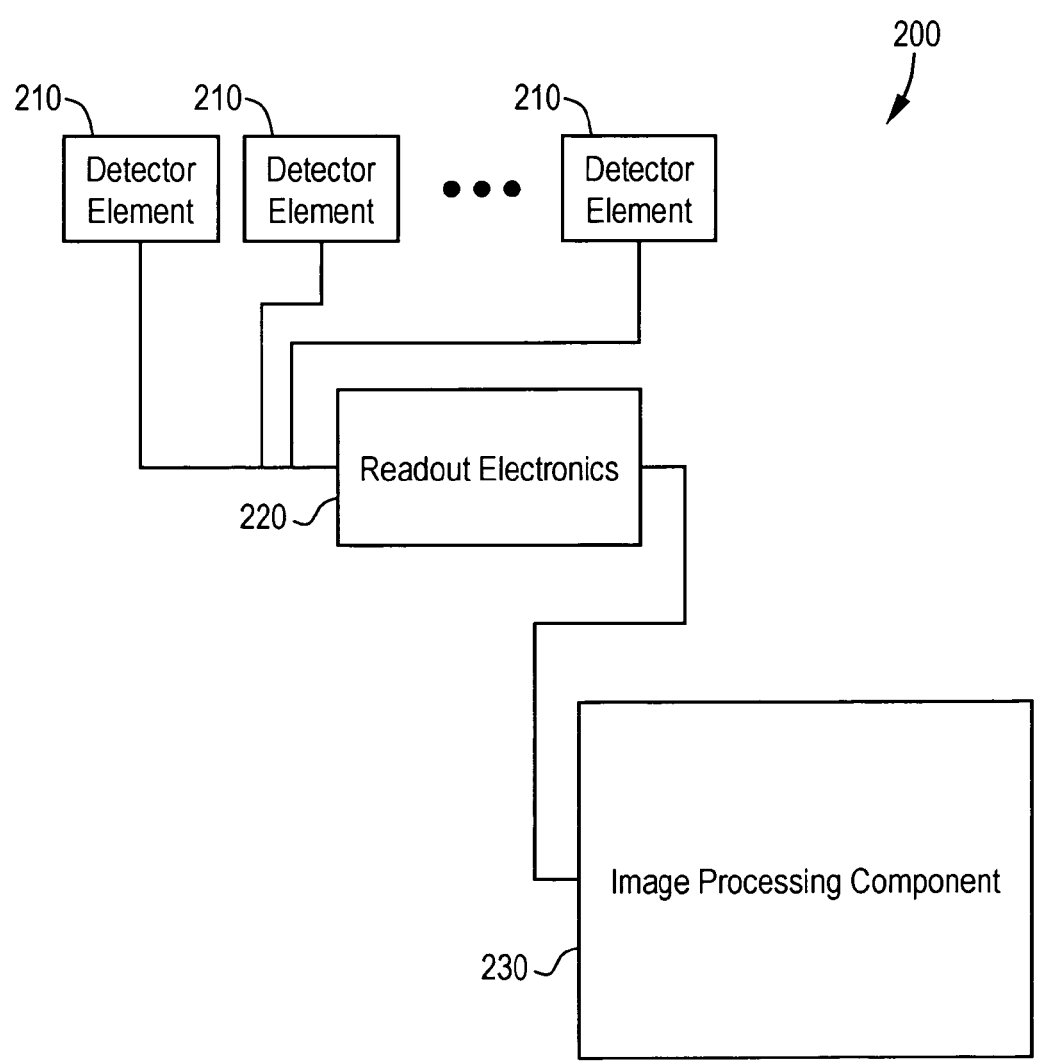
FIG. 2 illustrates a detector in an imaging system used in accordance with an embodiment of the present invention.

FIG. 2 illustrates a detector 200 in an imaging system used in accordance with an embodiment of the present invention. The detector 200 may be similar to the detector 120, described above, for example. The detector 200 includes detector elements 210 and readout electronics 220. In addition, the detector 200 may include an image processing component 230. The components of the detector 200 may be implemented separately or integrated in various forms. The components of the detector 200 may be implemented in hardware, software and/or firmware.

The detector elements 210 are in communication with the readout electronics 220. The readout electronics 220 are in communication with the image processing component 230.

The image processing component 230 may by physically and/or logically separate from the detector 200. The image processing component 230 may be similar to the image processing component 130, described above, for example.

In operation, the detector elements 210 are capable of detecting, for example, x-rays from an x-ray source. The source 110 generates energy such as x-rays 115. In an embodiment, the x-rays 115 pass through the object 140. In certain embodiments, a scintillator (not shown) is located between the source 110 and the detector 200. The x-rays 115 strike the scintillator. The scintillator emits light in response to x-rays absorbed. Light emitted by the scintillator activates the photodiodes in the detector elements 210 of the detector 200. The readout electronics 220 transmit the data from the detector 200 to the image processing component 230. Alternatively, the image processing component 230 may acquire the data from the readout electronics 220. The image processing component 230 may display the image. In an embodiment, the image processing component 230 may display x-ray images on video monitor. Alternatively, the image processing component 230 may store x-ray images in memory. The x-ray images may be examined on a computer, printed, e-mailed, faxed, or otherwise transmitted.

In certain embodiments, one or more components of the detector 200 may be affected by an electromagnetic field such as, for example, electromagnetic field 160. Components such as the detector element 210, readout electronics 220, and/or the wires connecting those components may be energized or de-energized by an electromagnetic field. This response to the presence of an electromagnetic field allows a field image to be acquired by the image processing component 230. This field image may contain data about the electromagnetic field 160. For example, the field image may represent the strength of the electromagnetic field 160 at one or more of the detector elements 210 of the detector 200.

Figure 3:
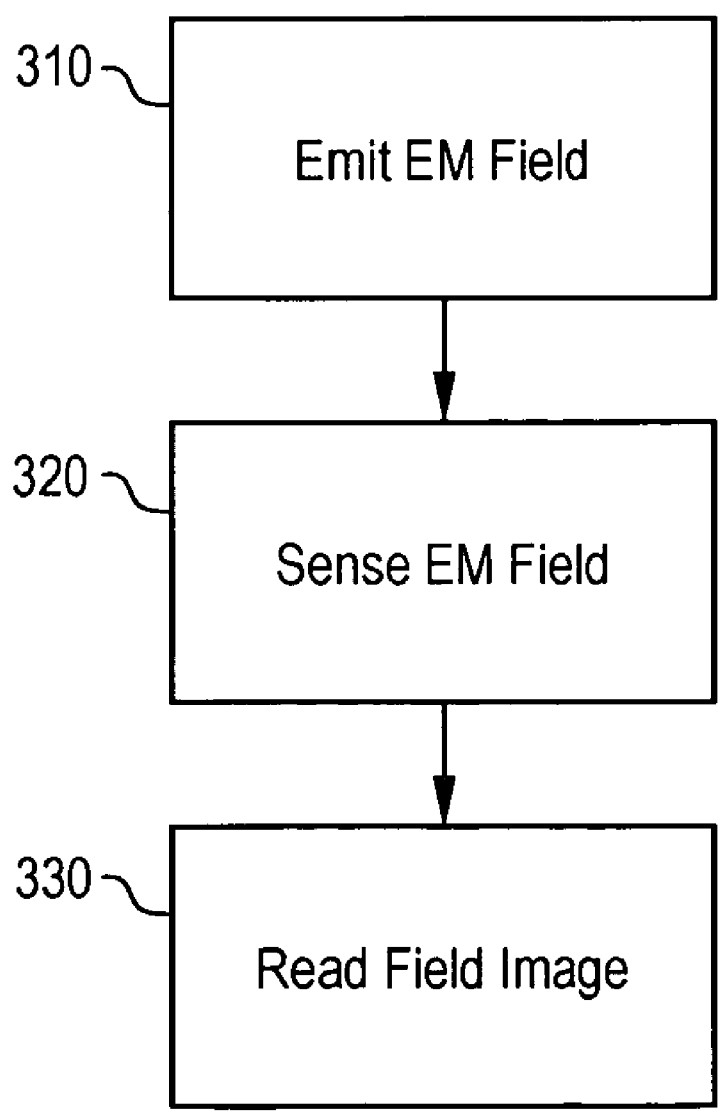
FIG. 3 illustrates a flow diagram for a method for detecting an electromagnetic field in an imaging system in accordance with an embodiment of the present invention.

FIG. 3 illustrates a flow diagram for a method 300 for detecting an electromagnetic field in an imaging system in accordance with an embodiment of the present invention. The method 300 includes the following steps, which will be described in more detail below. First, at step 310, an electromagnetic field is emitted. Then, at step 320, the detector senses the electromagnetic field. Next, at step 330, a field image is read. The method 300 is described with reference to elements of the system 100 described above, but it should be understood that other implementations are possible.

First, at step 310, an electromagnetic field 160 is emitted by an electromagnetic transmitter 150. The electromagnetic transmitter 150 may be, for example, a surgical navigation device. The electromagnetic transmitter 150 may have a transmit mode and a non-transmit mode. In the transmit mode, the electromagnetic transmitter 150 emits the electromagnetic field 160. In the non-transmit mode, the electromagnetic transmitter 150 does not emit the electromagnetic field 160.

Then, at step 320, the detector 120 senses the electromagnetic field 160. The detector 120 may be, for example, a flat panel detector, such as an amorphous silicon flat panel x-ray detector and associated readout electronics, as described above. The detector 120 may sense the electromagnetic field 160 because, for example, one or more components of the detector 120 are susceptible to influence by the electromagnetic field 160.

Next, at step 330, a field image is read from the detector 120. The field image may be based in part on the electromagnetic field sensed by the detector 120. The field image may represent, for example, the strength of the electromagnetic field emitted at step 310 at one or more of the detector elements of the detector 120. In an embodiment, the field image is coordinated to be read when the electromagnetic transmitter 150 is in a transmit mode. Alternatively, in an embodiment, the field image is coordinated to be read when the electromagnetic transmitter 150 is in a non-transmit mode. The field image may be read when no energy is being emitted by the source 110. For example, the field image may be read when no x-rays 115 are emitted by the source 110. In certain embodiments, the field image may be read when an object 140 is positioned in the imaging system 100. In certain embodiments, the field image may be read when no object 140 is present. In certain embodiments, steps 320 and 330 may occur simultaneously. That is, the electromagnetic field 160 may be sensed by the detector 120 as the field image is read from the detector 120.

In certain embodiments, the position of at least one of a surgical device, instrument, and/or tool is determined. The position may be determined based at least in part on the field image. For example, the field image may indicate a distortion or interference in the electromagnetic field that may be used to derive the position of a surgical instrument that may have a coil attached to it. As another example, data from the field image may be used in conjunction with other data from another source such as an electromagnetic receiver, for example, to improve the accuracy of a surgical navigation system.

In certain embodiments, an object image may be used to determine the location of an object made of metal and/or other material capable of distorting electromagnetic fields. For example, based at least in part on the absorption of x-rays indicated in an object image, the presence of metal may determined. The location of the metal in the object image may then be used to correlate and/or correct for distortions in the electromagnetic field detected in a field image, for example. In an embodiment, the model of the electromagnetic environment used by a surgical navigation system may be adjusted based at least in part on the object image and/or the field image. For example, when metal is detected and characteristics such as its position are determined using an object image, the object image may be used to interpret a field image to determine the effect and/or characteristics of the metal on the electromagnetic environment. Then, the electromagnetic model used by a surgical navigation system may be updated to compensate and/or account for the presence of the object causing distortions in the electromagnetic field utilized by the surgical navigation system.

In certain embodiments, an object image is read from the detector 120. The object image may be based in part on, for example, x-rays 115 emitted by a source 110. When no x-ray energy 115 or electromagnetic field 160 is incident on the imaging system 100 and an object image is read from the detector 120, the object image is typically referred to as a "dark" image. In certain embodiments, an object 140 is positioned in the imaging system 100. Some of the x-rays 115 may pass through the object 140 and be detected by the detector 120. The detected x-rays may be used to form the object image. In an embodiment, the energy detected at the detector 120 is representative of the structure of the object 140. In an embodiment, the object image is coordinated to be read when the electromagnetic transmitter 150 is in a transmit mode. Alternatively, in an embodiment, the object image is coordinated to be read when the electromagnetic transmitter 150 is in a non-transmit mode.

In certain embodiments, the object image is adjusted. The object image may be adjusted based in part on the field image. For example, if the field image indicates the presence of metal in the object 140 then the object image may be adjusted by an algorithm to account for the presence of metal in the object 140 being imaged. The algorithm may be an image processing algorithm such as a metal artifact reduction algorithm. In addition, the field image may be used to adjust the object image to account for distortions or artifacts caused by the electromagnetic field, for example. As another example, the field image may provide additional data that may be merged with an object image to create a multi-modality image ("image fusion"). As another example, "inverse scattering" may be utilized with one or more field images to reconstruct the object to be imaged, based on the electromagnetic field data in the field image(s) alone.

In an embodiment, the field image may be used to improve the accuracy of a surgical navigation system, for example. As an example, the field image may reveal unexpected distortions in the electromagnetic field that may result in misinterpretations of the surgical navigation receiver data. With data regarding these unexpected distortions provided by the field image, corrections may be made to the receiver data of the surgical navigation system, improving, for example, accuracy.

As mentioned above, certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Figure 4:
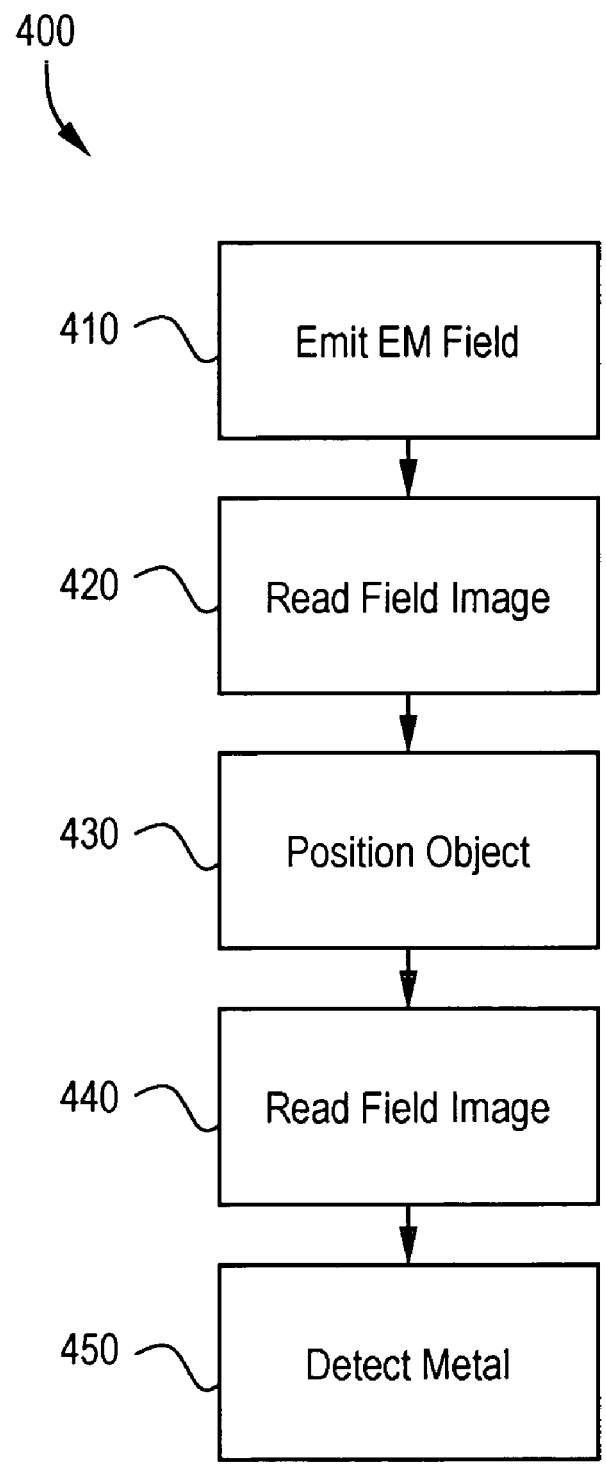
FIG. 4 illustrates a flow diagram for a method for improving image quality in an imaging system in accordance with an embodiment of the present invention.

FIG. 4 illustrates a flow diagram for a method 400 for improving image quality in an imaging system in accordance with an embodiment of the present invention. The method 400 includes the following steps, which will be described below in more detail. First, at step 410, an electromagnetic field is emitted. Then, at step 420, a first field image is read. Next, at step 430, an object is positioned. At step 440, a second field image is read. Then, at step 450, metal is detected. The method 400 is described with reference to elements of the system 100 described above, but it should be understood that other implementations are possible.

First, at step 410, an electromagnetic field is emitted. The electromagnetic field 160 may be emitted by, for example, an electromagnetic transmitter 150. The electromagnetic transmitter 150 may be, for example, a surgical navigation device. The electromagnetic transmitter 150 may have a transmit mode and a non-transmit mode. In the transmit mode, the electromagnetic transmitter 150 emits the electromagnetic field 160. In the non-transmit mode, the electromagnetic transmitter 150 does not emit the electromagnetic field 160.

Then, at step 420, a first field image is read. The first field image may be read from a detector 120. The detector 120 may be, for example, an amorphous silicon flat panel x-ray detector. The first field image may be based in part on the electromagnetic field sensed by the detector 120. The first field image may represent, for example, the strength of the electromagnetic field emitted at step 410 at one or more of the detector elements of the detector 120.

Next, at step 430, an object is positioned. The object 140 may be positioned in front of the detector 120. As an example, the object may be positioned between the source 110 and the detector 120. The object 140 may be, for example, a patient or a calibration tool. The object 140 may contain metal.

At step 440, a second field image is read. The second field image may be read from a detector 120. The detector 120 may be, for example, an amorphous silicon flat panel x-ray detector. The second field image may be based in part on the electromagnetic field sensed by the detector 120. The second field image may represent, for example, the strength of the electromagnetic field emitted at step 410 at one or more of the detector elements of the detector 120.

Then, at step 450, metal is detected. Metal in the object 140 being imaged may be detected by, for example, comparing the first field image and the second field image. This may be accomplished by a technique such as taking the difference between the first field image and the second field image, for example. As another example, a difference algorithm or other method may be used to detect the presence of metal. Metal, as used here, may include other materials capable of distorting electromagnetic fields in the object being imaged can result in artifacts or distortions in the image.

In an embodiment, an object image may be read from the detector 120. The object image may be based in part on, for example, x-rays 115 emitted by a source 110. For example, the object image may be an x-ray image. Some of the x-rays 115 may pass through the object 140 and be detected by the detector 120. The detected x-rays may be used to form the object image. In an embodiment, the object image is coordinated to be read when the electromagnetic transmitter 150 is in a transmit mode. Alternatively, in an embodiment, the object image is coordinated to be read when the electromagnetic transmitter 150 is in a non-transmit mode.

In certain embodiments, the object image may be processed. The object image may be adjusted based in part on the field image. For example, if one or both of the first and second field images indicates the presence of metal in the object 140 then the object image may be adjusted by an algorithm to account for the presence of metal in the object 140 being imaged. The algorithm may be an image processing algorithm such as a metal artifact reduction algorithm. Metal may be detected by, for example, examining the difference between the first and second field images. In addition, the first and/or second field image may be used to adjust the object image to account for distortions or artifacts caused by the electromagnetic field. For example, the object image may be processed by an image processing component 130. As another example, the object image may be processed with a metal artifact reduction algorithm. In an embodiment, the processing of the object image occurs when metal is detected in the object 140.

As mentioned above, certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Thus, certain embodiments of the present invention provide a way to detect electromagnetic fields so that distortions and artifacts caused by such fields can be compensated for. Certain embodiments of the present invention provide a way to determine when metal is present in the object being imaged so that techniques such as metal artifact reduction algorithms may be utilized.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for detecting an electromagnetic field in an imaging system, said method including:
   emitting an X-ray from an X-ray source and through an object;
   detecting the X-ray at an imaging system detector;
   reading an object image of the object based on the X-ray detection by the imaging system detector;
   emitting an electromagnetic field with an electromagnetic transmitter;
   sensing a scattered electromagnetic field with the imaging system detector in the direction of X-ray, the imaging system detector configured to read a field image from electromagnetic field data representing information about the scattered electromagnetic field sensed by the imaging system detector;
   reading a field image from the imaging system detector based at least in part on the electromagnetic field; and
   using the field image to identify a specific area in the object image that is affected by metal in the object.

2. The method of claim 1, wherein the imaging system detector is an amorphous silicon flat panel x-ray detector.

3. The method of claim 1, further including determining the position of at least one of a surgical device, instrument, and tool based at least in part on the field image.

4. The method of claim 1, wherein the electromagnetic transmitter has a transmit mode and a non-transmit mode, the electromagnetic transmitter emitting the electromagnetic field when in the transmit mode, and the electromagnetic transmitter not emitting the electromagnetic field when in the non-transmit mode.

5. The method of claim 4, wherein the reading of the field image is coordinated to occur when the electromagnetic transmitter is in the transmit mode.

6. The method of claim 4, wherein the reading of the object image is coordinated to occur when the electromagnetic transmitter is in the non-transmit mode.

7. The method of claim 4, further including adjusting an electromagnetic model of a surgical navigation system based at least in part on the field image and the object image.

* * * * *